(12) United States Patent
Gonzalez

(10) Patent No.: US 11,786,403 B2
(45) Date of Patent: Oct. 17, 2023

(54) OPHTHALMIC LASER DELIVERY APPARATUS USING MEMS MICROMIRROR ARRAYS FOR SCANNING AND FOCUSING LASER BEAM

(71) Applicant: AMO Development, LLC, Santa Ana, CA (US)

(72) Inventor: Javier G. Gonzalez, Palo Alto, CA (US)

(73) Assignee: AMO Development, LLC, Irvine, CA (US)

( * ) Notice: Subject to any disclaimer, the term of this patent is extended or adjusted under 35 U.S.C. 154(b) by 301 days.

(21) Appl. No.: 17/031,793

(22) Filed: Sep. 24, 2020

(65) Prior Publication Data

US 2021/0015667 A1 Jan. 21, 2021

Related U.S. Application Data

(62) Division of application No. 15/793,851, filed on Oct. 25, 2017, now Pat. No. 10,786,389.

(60) Provisional application No. 62/413,370, filed on Oct. 26, 2016.

(51) Int. Cl.
 *A61F 9/008* (2006.01)
 *G02B 26/08* (2006.01)
 (Continued)

(52) U.S. Cl.
 CPC .......... *A61F 9/00804* (2013.01); *A61F 9/008* (2013.01); *A61F 9/00817* (2013.01);
 (Continued)

(58) Field of Classification Search
 CPC .. A61F 9/008; A61F 9/00802; A61F 9/00804; A61F 9/00825;
 (Continued)

(56) References Cited

U.S. PATENT DOCUMENTS

| | | | | |
|---|---|---|---|---|
| 5,624,437 A | * | 4/1997 | Freeman | A61F 9/00817 606/5 |
| 5,720,894 A | | 2/1998 | Neev et al. | |
| | | (Continued) | | |

FOREIGN PATENT DOCUMENTS

WO  2012160005 A1  11/2012

OTHER PUBLICATIONS

International Search Report and Written Opinion for Application No. PCT/US2017/058360, dated Jan. 8, 2018, 13 pages.

*Primary Examiner* — Ahmed M Farah
(74) *Attorney, Agent, or Firm* — Johnson & Johnson Surgical Vision, Inc.

(57) ABSTRACT

In a laser delivery system for an ophthalmic laser surgery system, a laser beam scanner employs a single or two MEMS micromirror arrays. Each micromirror in the array is capable of being independently actuated to rotate to desired angles. In one embodiment, one or two micromirror arrays are controlled to scan a laser beam in two directions. In another embodiment, a micromirror array is controlled to both correct optical aberrations in the laser beam and scan the laser beam in two directions. In yet another embodiment, a micromirror array is controlled to cause the laser beam to be focused to multiple focal spots simultaneously and to scan the multiple focal spot simultaneously. The ophthalmic laser surgery system also includes an ultrashort pulse laser, a laser energy control module, focusing optics and other optics, and a controller for controlling the laser beam scanner and other components of the system.

7 Claims, 3 Drawing Sheets

(51) Int. Cl.
*G02B 26/10* (2006.01)
*G02B 30/50* (2020.01)
*G02B 27/18* (2006.01)
*G02B 27/28* (2006.01)

(52) U.S. Cl.
CPC ....... *G02B 26/0833* (2013.01); *G02B 26/101* (2013.01); *G02B 30/50* (2020.01); *A61F 2009/00872* (2013.01); *A61F 2009/00897* (2013.01); *G02B 27/18* (2013.01); *G02B 27/285* (2013.01)

(58) Field of Classification Search
CPC .. A61F 2009/00844; A61F 2009/00851; A61F 2009/00872; A61F 2009/00897; G02B 26/08; G02B 26/0816; G02B 26/0833; G02B 26/10; G02B 26/101; G02B 26/12
USPC .................. 606/4, 5, 10–12, 17, 18
See application file for complete search history.

(56) References Cited

U.S. PATENT DOCUMENTS

| | | |
|---|---|---|
| 5,957,915 A | 9/1999 | Trost |
| 5,984,916 A | 11/1999 | Lai |
| 6,019,472 A | 2/2000 | Koester et al. |
| 6,454,761 B1 | 9/2002 | Freedman |
| 7,655,002 B2 | 2/2010 | Myers et al. |
| 7,717,907 B2 | 5/2010 | Ruiz et al. |
| 8,262,646 B2 | 9/2012 | Frey et al. |
| 8,350,183 B2 | 1/2013 | Vogel et al. |
| 8,382,745 B2 | 2/2013 | Naranjo-Tackman et al. |
| 8,414,564 B2 | 4/2013 | Goldshleger et al. |
| 2011/0319873 A1 | 12/2011 | Raksi et al. |
| 2011/0319875 A1 | 12/2011 | Loesel et al. |
| 2014/0081247 A1* | 3/2014 | Heiberger ............... A61F 9/008 606/4 |
| 2014/0088573 A1* | 3/2014 | Heiberger ............ A61B 3/1015 351/200 |
| 2015/0085254 A1 | 3/2015 | Sramek et al. |
| 2015/0173608 A1 | 6/2015 | Papac et al. |
| 2015/0202083 A1* | 7/2015 | Takeda .................. A61B 18/20 606/4 |
| 2015/0272782 A1* | 10/2015 | Schuele ............... A61B 3/1173 606/5 |
| 2016/0008169 A1* | 1/2016 | Yu .......................... A61B 3/102 606/4 |
| 2016/0183782 A1* | 6/2016 | Yu .......................... A61B 90/20 606/4 |
| 2019/0175402 A1 | 6/2019 | Eil et al. |
| 2019/0314194 A1 | 10/2019 | Artsyukhovich et al. |

\* cited by examiner

OPHTHALMIC LASER DELIVERY APPARATUS USING MEMS MICROMIRROR ARRAYS FOR SCANNING AND FOCUSING LASER BEAM

RELATED APPLICATIONS

This application claims priority to and is a divisional of U.S. patent application Ser. No. 15/793,851, filed Oct. 25, 2017, which claims priority to, and the benefit of, under U.S.C. § 119(e) of U.S. Provisional Appl. No. 62/413,370, filed on Oct. 26, 2016, which is incorporated herein by reference in its entirety.

BACKGROUND OF THE INVENTION

Field of the Invention

This invention relates to a laser delivery system for ophthalmic procedures, and in particular, it relates to such a laser delivery system that employs MEMS micromirror arrays for scanning and focusing the laser beam.

Description of Related Art

Ophthalmic laser surgery systems use a laser delivery system to deliver a laser beam generated by a laser into a patient's eye. The laser delivery system focuses the laser beam and scans the focal spot over an area or volume of the eye (referred to as the treatment area or region) to achieve desired therapeutic effects, such as photoalteration of the eye tissues. FIG. 1 is a block diagram that schematically illustrates an ophthalmic laser surgery system 10. The system 10 includes a laser 14 capable of generating a pulsed laser beam 18, an energy control module 16 for controlling and varying the pulse energy of the pulsed laser beam 18, a scanner 20 for scanning the laser beam, focusing optics 28 for directing the pulsed laser beam 18 on the surface of or within the region 12 (e.g., sub-surface) of the patient's eye, an imaging system 34 for displaying a real-time digital image of the patient's eye and providing other information, a controller 22, and a user interface 32 for the operator to interact with the system. The system 10 also includes a beam splitter 26 and a detector 24 coupled to the controller 22 to provide a feedback control mechanism for the pulsed laser beam 18. The laser 14 may be, for example, an ultrashort pulse laser, e.g. a femtosecond laser that can output a pulsed laser beam having a pulse width in the picosecond to femtosecond range. In some systems, some components, such as the beam splitter 26 and detector 24, may be omitted; some other systems may include additional components not shown in FIG. 1, such as range finding system, etc.

In conventional laser delivery systems, the scanner 20 uses a pair of scanning mirrors driven by galvanometers (referred to as galvo mirrors) to angularly deflect and scan the laser beam 18. Each galvo mirror scans the laser beam along one of the two orthogonal axes, so that the focal point 30 of the laser beam 18 may be scanned in two dimensions (e.g., the x-axis and the y-axis) in the focal plane of the system 10. Scanning along the third dimension, i.e., moving the focal plane along the optical axis (the z-axis), may be achieved by moving the focusing optics 28 along the optical axis. The laser focal spot is scanned in a desired scan pattern, for example, a raster pattern, a circular pattern, a spiral pattern, a sine wave pattern, etc.

FIG. 1A schematically illustrates a part of the scanner 20, showing one of the pair of galvo mirrors 20A, being rotatable around an axis perpendicular to the drawing sheet (as indicated by the double-arrowed arc), for scanning the laser focal spot along the x-axis. Note that the input light beam is typically a collimated beam, as schematically represented by three light rays in FIG. 1A, although only one ray is shown on the output side of FIG. 1A to avoid overcrowding. Another galvo mirror (not shown in FIG. 1A) scans the focal spot along the y-axis (perpendicular to the drawing sheet in this illustration).

The controller 22, which includes at least a processor and a memory storing computer executable programs, communicates with the scanner 20 and optionally also the focusing optics 28 to direct a focal point 30 of the pulsed laser beam onto or into the eye. The two galvo mirrors in the scanner 20 may be controlled via a motion control system, such as a closed-loop control system.

SUMMARY

In conventional ophthalmic laser systems described above, in which the laser delivery system uses actuation of galvanometers-driven mirrors to scan the laser beam in the x and y directions, the galvo mirrors are relatively large and have relatively large inertia that may prevent large accelerations during execution of the laser scan. For example, the galvo mirror that executes the laser scan must decelerate before the scan trajectory switches direction. The larger the moments of inertia of the galvo mirrors, the longer such deceleration or acceleration requires. As a result, a particular galvo mirror system has an inherent maximum acceleration that limits the scan patterns and speed that can be executed with the galvo mirror system.

Additionally, in conventional ophthalmic laser systems described above, each of the two scanning mirrors that control laser delivery in the x, y dimensions is typically a flat mirror. A single flat mirror cannot correct wavefront aberrations that are invariably present in laser beams produced by the various optical components of the system. Aberrations in the laser delivery system can result in undesirably large focal spot sizes (i.e., the laser beam cannot be precisely focused to a small focal spot). The focal spot size also tends to depend on the x-y position of the focal spot; the focal spot typically becomes larger at locations farther away from the optical axis of the eye. Moreover, aberrations of this type become more apparent at larger depth (from the anterior surface of the eye) of the laser treatment region.

One consequence of these aberrations is the spatial variation of the laser pulse energy threshold for bubble formation to achieve photodisruption of the eye tissue. Bubble formation requires a threshold level of power density or pulse energy density (i.e. power or pulse energy per unit area). The pulse energy threshold relates directly to the minimum required energy to cut the tissue. Aberration increases the focal spot size and reduces energy density or power density, so higher pulse energy will be required for bubble formation. In one example, data show that at a target depth or 12 mm, which is still shallower than most posterior surfaces of crystalline lenses, pulse energy required for bubble formation may be many times higher for peripheral areas (e.g. 7 mm from the optical axis) than for the center areas near the optical axis. Thus, the laser pulse energy levels have to be set sufficiently high for the entire treatment area of the eye to ensure that peripheral regions receive a pulse energy density above the bubble formation threshold. This means delivering far more energy to the eye than strictly required, increasing unnecessarily the laser exposure to the patient. Moreover, such energy requirement could in fact preclude certain procedures (for example, sideport incisions in some cases) because they would not be compliant with laser safety regulations.

Accordingly, the present invention is directed to a laser delivery system for an ophthalmic laser system that substantially obviates one or more of the problems due to limitations and disadvantages of the related art.

An object of the present invention is to provide an ophthalmic laser delivery system that has improved acceleration of the scan pattern by reducing the inertia of the scanning mirrors.

Another object of the present invention is to provide an ophthalmic laser delivery system that achieves improved focusing of the laser beam.

Another object of the present invention is to provide an ophthalmic laser delivery system that can simultaneously focus the laser beam to multiple focal spots.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and/or other objects, as embodied and broadly described, the present invention provides an ophthalmic laser delivery system for delivering a pulsed laser beam generated by a laser to a patient's eye, which includes: a laser beam scanner for reflecting an input laser beam to generate one or more output laser beams and scanning the output laser beams in two orthogonal directions, the laser beam scanner including at least one micromirror array, the micromirror array including a plurality of micromirrors forming a two-dimensional array, the plurality of micromirrors capable of being individually controlled to rotate to different angles; optics for direction the pulsed laser beam from the laser to the laser beam scanner as the input laser beam and directing the output laser beams from the laser beam scanner to the patient's eye; and a controller coupled to the laser beam scanner for controlling a rotation of each of the plurality of micromirrors of the at least one micromirror array, wherein the laser beam scanner, as controlled by the controller, cooperates with the optics to focus the pulsed laser beam to one or more focal spots in the patient's eye and to scan the one or more focal spots according to a predefined scan pattern. The micromirror array may be a MEMS (micro-electro-mechanical system) structure.

In some embodiments, the laser beam scanner includes two micromirror arrays disposed in series along an optical path of the laser beam, wherein each micromirror in each micromirror array rotates around only one rotation axis, the rotation axes of all micromirrors in the same micromirror array being parallel to each other, and the rotation axes of the micromirrors in the two micromirror arrays being perpendicular to each other.

In some embodiments, the laser beam scanner includes a single micromirror array, wherein each micromirror in the micromirror array rotates around two orthogonal rotation axes, the respective one of the two rotation axes of all micromirrors in the micromirror array being parallel to each other.

In some embodiments, the controller controls the rotation angles of the plurality of micromirrors of the micromirror array to generate a focal spot of the laser beam at a specified position in the patient's eye that has a size smaller than a size of a focal spot generated at the specified position when all micromirrors of the micromirror array are rotated to identical angles.

In some embodiments, for any given focal spot position in the scan pattern, the rotation angles of at least some of the micromirrors are different from the rotation angles of at least some other micromirrors.

In some embodiments, the controller controls the rotation angles of the plurality of micromirrors of the micromirror array to simultaneously generate a plurality of focal spots of the laser beam in the patient's eye and to simultaneously scan the plurality of focal spots.

In another aspect, the present invention provides an ophthalmic laser delivery method for delivering a pulsed laser beam generated by a laser to a patient's eye, which includes: directing the pulsed laser beam from the laser to a laser beam scanner, the laser beam scanner including at least one micromirror array, the micromirror array including a plurality of micromirrors forming a two-dimensional array, the plurality of micromirrors capable of being individually controlled to rotate to different angles; using a controller coupled to the laser beam scanner, controlling a rotation of each of the plurality of micromirrors of the at least one micromirror array, to reflect the pulsed laser beam to generate one or more output laser beams and to scan the output laser beams in two orthogonal directions according to a predefined scan pattern; and directing the output laser beams from the laser beam scanner to the patient's eye to form one or more focal spots that are scanned within an arear of the eye.

It is to be understood that both the foregoing general description and the following detailed description are exemplary and explanatory and are intended to provide further explanation of the invention as claimed.

DETAILED DESCRIPTION OF PREFERRED EMBODIMENTS

Embodiments of the present invention provides a laser delivery system for an ophthalmic laser surgery system, in which the x-y beam scanner employs a single or two micromirror arrays micro-fabricated using MEMS (micro-electro-mechanical system) technology.

MEMS micromirror arrays are known and have been used in projection display systems and other technologies. The micromirror array is fabricated on a silicon wafer; each micromirror has a reflective surface and is suspended by torsion bars, with actuators for controlling the angle of the reflective surface relative to the fixed base on which the mirror is mounted. In some MEMS micromirror arrays, each micromirror can only rotates around one axis. In some other MEMS micromirror arrays, each micromirror can rotate around two orthogonal axes independently; the corresponding rotation axes of all micromirrors in the array are parallel to each other. Actuation mechanisms for micromirrors include electrostatic actuation using parallel plates or comb drives, electromagnetic actuation, magnetic actuation, piezoelectric actuation, thermal bimorph actuation, etc. Such MEMS micromirror arrays and their fabrication process are generally known.

Figure 1:
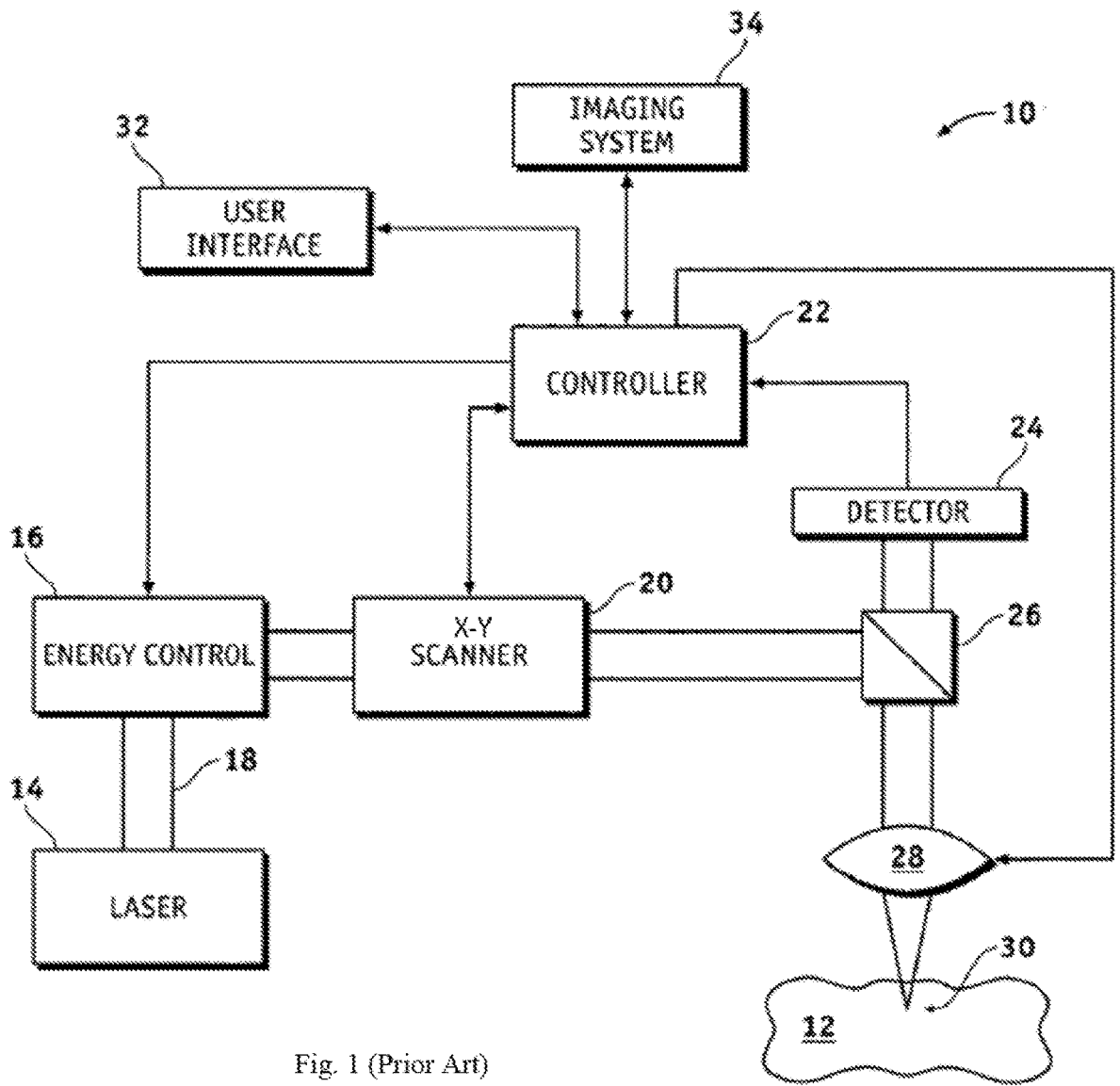
FIGS. 1 and 1A schematically illustrate a conventional ophthalmic laser surgery system in which the x-y beam scanner employs two galvo mirrors.
Figure 1A:
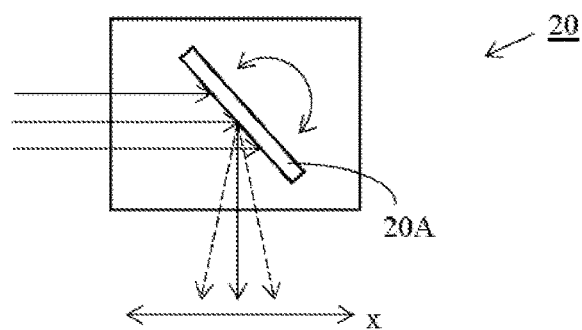
Figure 2:
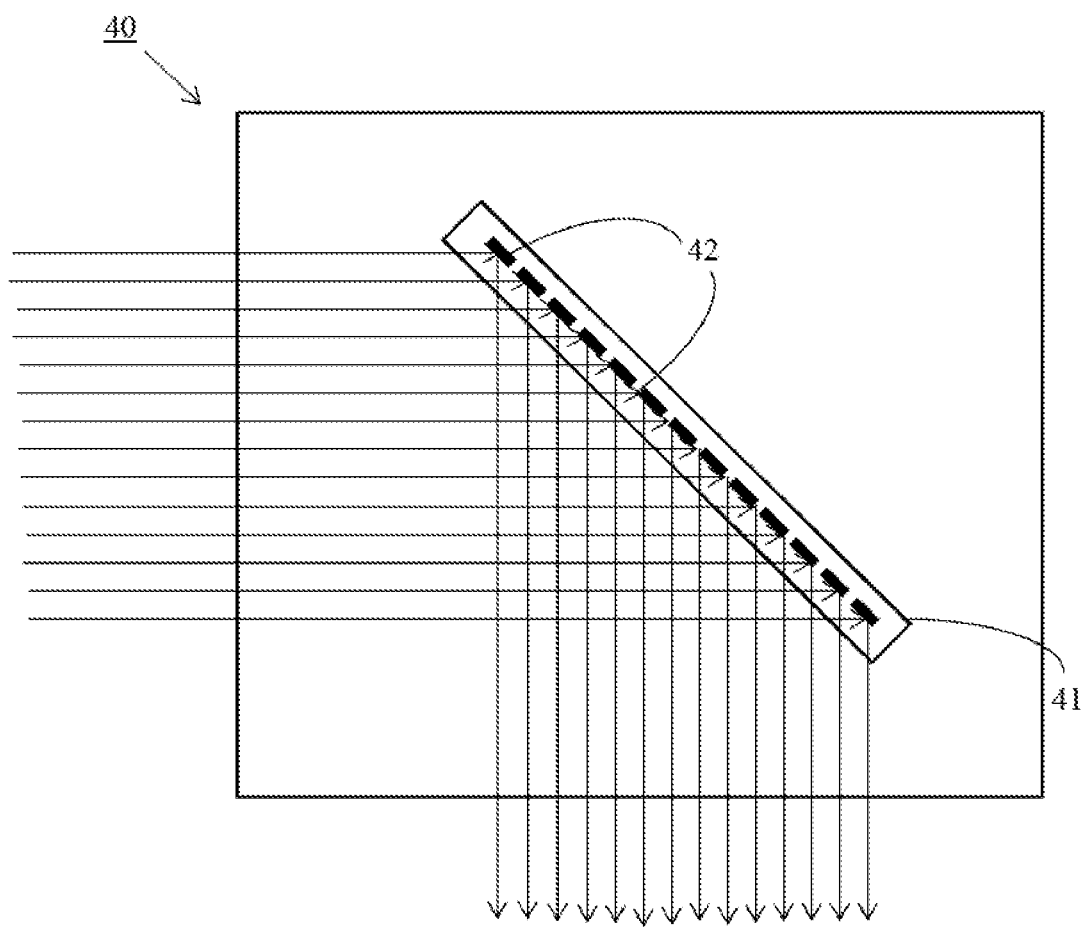
FIG. 2 schematically illustrates an x-y beam scanner for an ophthalmic laser delivery system which employs one or a pair of MEMS micromirror arrays according to an embodiment of the present invention.

FIG. 2 schematically illustrates a laser beam scanner 40 that employs one or two micromirror arrays 41 (only one is shown in FIG. 2). Each micromirror array 41 includes a two-dimensional array of micromirrors 41, as well as necessary drive circuitry (not shown in FIG. 2) to drive each micromirror. The beam scanner 40 replaces the scanner 20 in the laser system shown in FIG. 1. As shown in FIG. 2, the input beam impinges on the multiple individual micromirrors 42 of the micromirror array 41 and is reflected by them. Each mirror is controlled by its actuating mechanism to rotate along one axis or two axes. The size of the micromirror arrays 41 is preferably approximately the same as that of the conventional galvo mirror 20A, the size being dependent on the size of the laser beam to be reflected, and each micromirror in the array being substantially smaller than the conventional galvo mirror.

The laser beam scanner 40 is coupled to the controller 22. The controller 22 in various embodiments of the present invention is different from the controller in conventional ophthalmic laser systems in that the controller in embodiments of the present invention contains computer programs to control the micromirror arrays 41 to execute various scanning modes. Embodiments of the present invention provide various configurations and scanning modes of the beam scanner 40, as controlled by the controller.

In a first embodiment, the beam scanner 40 employs two micromirror arrays 41, to scan the laser beam in the x-direction and the y-direction, respectively. The two arrays may have identical structures. In each micromirror array 41, each micromirrors 42 only rotates around one axis, and therefore scans the laser beam in one direction. The two arrays 41 are disposed in series along the optical path, but oriented such that their rotation axes are perpendicular to each other. In this embodiment, all micromirrors 42 in the same array 41 are controlled to rotate synchronously in identical manners; thus, all micromirrors are parallel to each other during scanning. When the input laser beam is a collimated beam, the beam is reflected by the individual micromirrors 42 of the array 41 to form a collimated output beam; as such, the micromirror arrays 41 in this embodiment do not correct the optical aberration present in the laser beam. The output laser beam from the scanner 40 is focused by the focusing optics 28 to a focal spot within the treatment area of the eye. The controller controls the rotation of the individual micromirrors of the two micromirror arrays 41 based on a predefined scan patter. As a result, the focal spot of the laser beam is scanned within the treatment area of the eye according to the predefined scan pattern.

An advantage of the beam scanner of the first embodiment is that because each micromirror 42 has a much smaller inertia as compared to conventional galvo mirrors, a higher maximum acceleration/deceleration rate of the beam scanner can be achieved, which improves the overall scan rate.

In a second embodiment, the beam scanner 40 employs a single micromirror array 41 in which each micromirror 42 has two independent orthogonal axes of rotation. The corresponding rotation axes of all micromirrors in the array are parallel to each other. Typically, a dual-axis micromirror has a fast axis and a slow axis. The micromirrors 42 are controlled to rotate around both axes to scan the laser beam in both the x-direction and the y-direction. In this embodiment, all micromirrors 42 in the array 41 are controlled to rotate synchronously in identical manners; thus, all micromirrors are parallel to each other during scanning. Thus, the micromirror array 41 reflects a collimated input laser beam to form a collimated output beam; as such, the micromirror array 41 in this embodiment does not correct the optical aberration present in the laser beam. The output laser beam from the scanner 40 is focused by the focusing optics 28 to a focal spot within the treatment area of the eye. The controller controls the rotation of the individual micromirrors of the micromirror array 41 based on a predefined scan patter. As a result, the focal spot of the laser beam is scanned within the treatment area of the eye according to the predefined scan pattern.

In a third embodiment, the beam scanner 40 employs a single micromirror array 41 in which each micromirror 42 has two axes of rotation. The individual micromirrors 42 in the array 41 are independently controlled to rotate to desired angles (around both axes) so as to correct the optical aberration in the laser beam.

Figure 3:
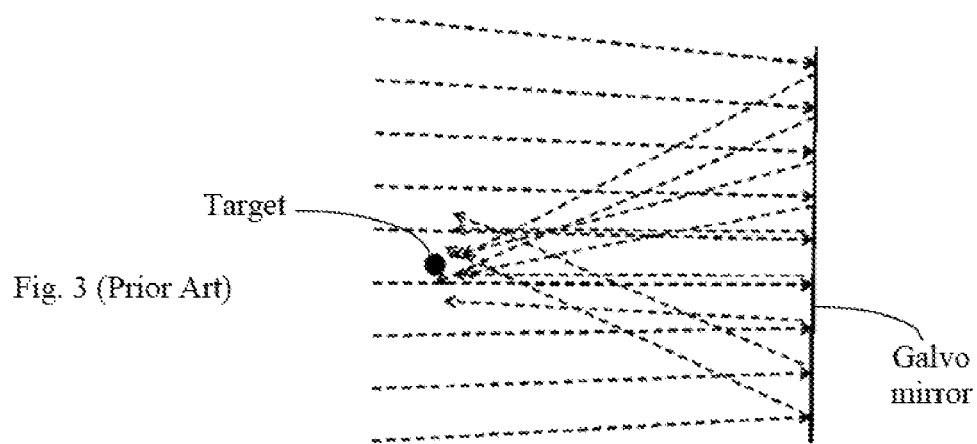
FIG. 3 schematically illustrates the effect of optical aberration when using a galvo mirror in a conventional beam scanner.
Figure 4:
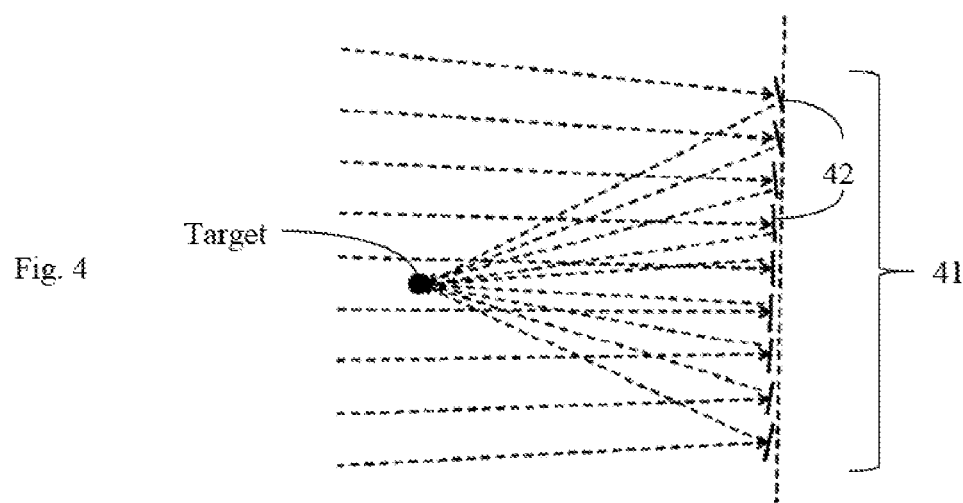
FIG. 4 schematically illustrates the principle of correction of optical aberration using a micromirror array in the beam scanner of the embodiment of FIG. 2.

FIGS. 3 and 4 schematically illustrate the effect of aberration correction by a micromirror array. FIG. 3 schematically illustrates a conventional galvo mirror; it schematically depicts a converging input light beam onto a single flat galvo mirror, and the converging beam, after reflection by the flat mirror, forms a focal spot of a relatively large size, due to the optical aberration present in the input light beam caused by of upstream optical elements. FIG. 4 schematically illustrates the same input light beam as reflected by a micromirror array 41, in which individual micromirrors 42 are independently controlled to desired angles around both rotation axes, such that the light beam, after reflection by the micromirror array, forms a focal spot smaller than that formed when a single galvo mirror is used (FIG. 3) or when all the micromirrors of the micromirror array are all parallel to each other (i.e. all rotated to the same angle). This way, the micromirror array 42 can correct optical aberrations caused by other optical components in the optical system.

It should be noted that FIGS. 3 and 4 are only intended to illustrate the principle of aberration correction by a micromirror array; the light beams depicted in these figures do not necessarily represent the configuration of an actual laser delivery system. In an actual laser delivery system, the input light to the micromirror array 41 is typically a collimated beam, which, as understood in the context of this embodiment, is a near parallel beam that may contain aberrations; the reflected beam is also a collimated beam but with reduced or corrected aberrations. In an actual laser delivery system, focusing optics 28 are typically used downstream of the beam scanner 20/40 to focus the collimated light to the treatment area of the patient's eye. Thus, preferably, the micromirror array 41 is controlled such that it reduces the combined optical aberrations of the entire optical system, so that the focal spot size obtained at the location of the patient's eye is reduced or minimized.

In the conventional system, a big contributing factor to the aberrations of the beam is that the system is not telecentric, because it has to galvo mirrors, i.e. for the x and y directions. Substituting the two galvo mirrors by a micromirror array can reduce or eliminate these aberrations.

As mentioned earlier, optical aberration typically causes the focal spot size to vary depending on its location, e.g. the distance of the focal spot from the optical axis. Thus, the micromirror array is preferably controlled such that the focal spot size is minimized across the laser treatment area within the patient's eye.

To achieve this result, the required rotation angles of each micromirror that will minimize aberrations of the focal spot at each particular x-y location within the treatment area are determined. In practice, the required rotation angles of each micromirror may be determined for a discrete set of focal spot positions across the treatment area, and interpolated for other focal spot positions. The required rotation angles may be calculated by modeling the optical properties of the optical components of the system, or determined by an empirical method, e.g., by measuring the light intensity or wavefront of the actual focal spot and adjusting the rotation angles of the micromirrors to reduce the focal spot size, or obtained by a combination of the modeling and empirical approaches. The rotation angles obtained can be stored in a lookup table and used to perform scans.

It is noted that to achieve the result of aberration correction, for any given focal spot position, the required rotation angles of the micromirrors in the array are expected to be different from each other, or the required rotation angles of at least some of the micromirrors are different from the rotation angles of at least some other micromirrors.

The required rotation angles of each micromirror as a function of the desired focal spot position may be referred to as the calibration function of the micromirror array, denoted $C_i(p)$ where C represents the required rotation angles, i is an index of the micromirrors, and p is the location of the focal spot.

Once the calibration function of the micromirror array is obtained, a predefined scan pattern of the laser beam can be executed by controlling the rotation angles of each individual micromirror in the array as a function of time, based on the calibration function and the predefined laser beam scan pattern. In other words, based on the calibration function $C_i(p)$ and the focal spot position as a function of time, denoted $p(t)$, the rotation angles as a function of time, denoted $C_i(t)$, can be calculated. As a result, the focal spot of the laser beam is scanned over the treatment area of the eye according to the predefined scan pattern.

Figure 5:
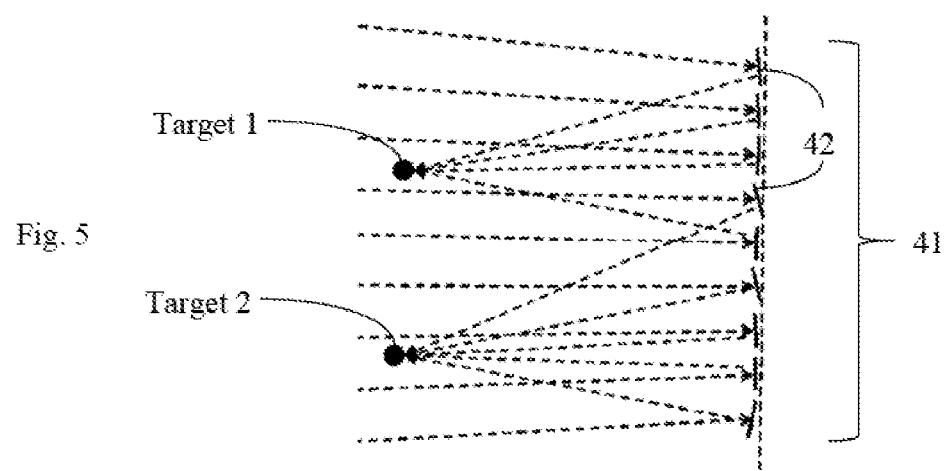
FIG. 5 schematically illustrates the principle of producing multiple simultaneous focal points using a micromirror array in the beam scanner of the embodiment of FIG. 2.

In a fourth embodiment, the micromirror array or arrays of the beam scanner 40 are controlled to focus the laser beam simultaneously to multiple focal spots. FIG. 5 schematically illustrates the principle of this embodiment. As shown in FIG. 5, micromirrors 42 in different parts of the array 41 are used to simultaneously focus the laser light to different locations. In other words, one subset of micromirrors collectively focus the laser light impinging on them to one focal point, another subset of micromirrors collectively focus the laser light impinging on them to another focal point, etc. The micromirror array may be divided into these subsets of micromirrors in any suitable way.

It should be noted that FIG. 5 is only intended to illustrate the principle of simultaneous focusing to multiple focal points by the micromirror array; the light beams depicted in this figure do not necessarily represent the configuration of an actual laser delivery system. In an actual laser delivery system, the input light to the micromirror array 41 is typically a collimated beam; the output light of the micromirror array simultaneously contains multiple collimated beams in slightly different directions, and the multiple collimated beams are focused by the focusing optics 28 to simultaneously form multiple focal spots in the treatment area of the eye.

The fourth embodiment may be implemented in a way that does not provide aberration correction for the focal spots, in a manner described above for the second embodiment, or it may be implemented in a way that provides aberration correction for each focal spot, in a manner described above for the third embodiment.

Using this embodiment, laser treatment can be delivered to multiple locations in the patient's eye simultaneously, which can speedup treatment. For example, in some ophthalmic procedures, the scan pattern of the pulsed laser beam is a raster pattern having multiple lines, each line corresponding to a scan in the "fast" direction of the scanner, and the multiple lines are scanned sequentially. Using a scanner according to this embodiment of the invention, multiple focal spots that are spaced apart in the "slow" direction can be scanned simultaneously in the "fast" direction to form multiple scan lines in one scan. Using multiple simultaneous focal spots can also make the design of the scan pattern more flexible.

In the above embodiments, the control of the individual mirror arrays of the beam scanner 40 is performed by the controller 22. The controller 22 includes at least a processor and a memory storing computer readable programs which are executed to control the micromirror array or arrays of the beam scanner 40. A separate controller may alternatively be provided to control the micromirror arrays of the scanner.

The laser system described above may be used for various ophthalmic procedures, such as laser cataract surgery where the laser energy is used to fragment the cataractous lens, in flap formation for LASIK (Laser Assisted In Situ Keratomileusis) where the laser energy is used to make incisions within corneal tissue to form a flap, etc. In particular, within cataract surgery, the laser system may be used to perform corneal cuts. An arcuate cut, for instance, is a 3-dimensional raster scan, that produces a plane that cuts the cornea. Other examples include primary and sideport incisions.

It will be apparent to those skilled in the art that various modification and variations can be made in the laser delivery apparatus of an ophthalmic laser system and related methods of the present invention without departing from the spirit or scope of the invention. Thus, it is intended that the present invention cover modifications and variations that come within the scope of the appended claims and their equivalents.

What is claimed is:

1. An ophthalmic laser delivery method for delivering a pulsed laser beam generated by a laser to a patient's eye, comprising:

directing the pulsed laser beam from the laser to a laser beam scanner, the laser beam scanner including at least one micromirror array, the micromirror array including a plurality of micromirrors forming a two-dimensional array, the plurality of micromirrors capable of being individually controlled to rotate to different angles;

using a controller coupled to the laser beam scanner, controlling a rotation of each of the plurality of micromirrors of the at least one micromirror array, to reflect the pulsed laser beam to generate one or more output laser beams and to scan the output laser beams in two orthogonal directions according to a predefined scan pattern; and directing the output laser beams from the laser beam scanner to the patient's eye to form one or more focal spots that are scanned within an arear of the eye.

2. The ophthalmic laser delivery method of claim 1, wherein the laser beam scanner includes two micromirror arrays disposed in series along an optical path of the laser beam, wherein each micromirror in each micromirror array rotates around only one rotation axis, the rotation axes of all micromirrors in the same micromirror array being parallel to each other, and the rotation axes of the micromirrors in the two micromirror arrays being perpendicular to each other.

3. The ophthalmic laser delivery method of claim 1, wherein the laser beam scanner includes a single micromirror array, wherein each micromirror in the micromirror array rotates around two orthogonal rotation axes, the respective one of the two rotation axes of all micromirrors in the micromirror array being parallel to each other.

4. The ophthalmic laser delivery method of claim 3, wherein the controlling step includes controlling the rotation angles of the plurality of micromirrors of the micromirror array to generate a focal spot of the laser beam at a specified position in the patient's eye that has a size smaller than a size of a focal spot generated at the specified position when all micromirrors of the micromirror array are rotated to identical angles.

5. The ophthalmic laser delivery method of claim 3, wherein the controlling step includes controlling the rotation angles of the plurality of micromirrors of the micromirror array to generate a focal spot of the laser beam at a specified position in the patient's eye, and wherein the rotation angles of at least some of the micromirrors are different from the rotation angles of at least some other micromirrors.

6. The ophthalmic laser delivery method of claim 3, wherein the controlling step includes controlling the rotation angles of the plurality of micromirrors of the micromirror array to simultaneously generate a plurality of focal spots of the laser beam in the patient's eye and to simultaneously scan the plurality of focal spots.

7. The ophthalmic laser delivery method of claim 1, wherein each of the at least one micromirror array is a MEMS (micro-electro-mechanical system) structure.

* * * * *